United States Patent [19]

Moore

[11] Patent Number: 4,727,015

[45] Date of Patent: Feb. 23, 1988

[54] PHOTOGRAPHIC ELEMENT CONTAINING ORGANOSILANES

[75] Inventor: Christopher P. Moore, Harrow, United Kingdom

[73] Assignee: Eastman Kodak Company, Rochester, N.Y.

[21] Appl. No.: 248

[22] Filed: Jan. 2, 1987

[30] Foreign Application Priority Data

Jan. 15, 1986 [GB] United Kingdom ............ 8600933

[51] Int. Cl.$^4$ ..................... G03C 7/16; G03C 7/26
[52] U.S. Cl. ................. 430/377; 430/487; 430/543; 430/546; 430/550
[58] Field of Search ......... 430/159, 377, 373, 487, 430/543, 546, 550, 551

[56] References Cited

U.S. PATENT DOCUMENTS

| | | | |
|---|---|---|---|
| 4,264,720 | 4/1981 | Hamaoka et al. | 430/549 |
| 4,266,020 | 5/1981 | Sakai et al. | 430/551 |
| 4,346,165 | 8/1982 | Sawada et al. | 430/372 |

FOREIGN PATENT DOCUMENTS 2061540 5/1981 United Kingdom .

*Primary Examiner*—Paul R. Michl
*Assistant Examiner*—Patrick Doody
*Attorney, Agent, or Firm*—Harold E. Cole

[57] ABSTRACT

A photographic element comprising a support having thereon at least one silver halide emulsion layer having associated therewith a dye-forming coupler and an organosilane, nonhydrolyzable in an alkaline medium, wherein:

(a) one or two aryloxy groups are attached to the silicon atom of the silane either directly or indirectly through an alkylene group or an alkyleneoxy group, and (b) each aryloxy group is attached directly or indirectly through a single linking group to an aryl group substituted with a hydroxy, hydroxyalkoxy, organosilyloxy, organosilylalkoxy or organosilyloxyalkoxy group.

Use of the compounds provides an improvement in density and contrast.

14 Claims, No Drawings

PHOTOGRAPHIC ELEMENT CONTAINING ORGANOSILANES

This invention relates to a photographic element containing certain organosilanes for enhancing photographic color development. More particularly, it relates to the use of certain organosilanes for improving the density and contrast of dye images obtained by color development of incorporated-coupler photographic silver halide materials.

Images are commonly obtained in the photographic art by a coupling reaction between the development product of a silver halide color developing agent (i.e., oxidized aromatic primary amino developing agent) and a color forming compound commonly referred to as a coupler. The dye produced by coupling are indoaniline, azomethine, indamine or indophenol dyes, depending upon the chemical composition of the coupler and the developing agent. The subtractive process of color formation is ordinarily employed in multicolor photographic elements and the resulting image dyes are usually cyan, magenta and yellow dyes which are formed in or adjacent to silver halide layers sensitive to radiation complementary to the radiation absorbed by the image dye; i.e. silver halide emulsions sensitive to red, green and blue radiation.

The patent and technical literature is replete with references to compounds which can be used as couplers for the formation of photographic images. Preferred couplers which form cyan dyes upon reaction with oxidized color developing agents are phenols and naphthols. Representative couplers are described in the following patents and publications: U.S. Pat. Nos. 2,772,162, 2,895,826, 3,002,836, 3,034,892, 2,474,293, 2,423,730, 2,367,531, 3,041,236, 4,333,999 and "Farbkuppler-eine Literaturubersicht," published in Agfa Mitteilungen, Band II, pp. 156–175 (1961).

Preferred couplers which form magenta dyes upon reaction with oxidized color developing agent are pyrazolones, pyrazolotriazoles, pyrazolobenzimidazoles and indazolones. Representative couplers are described in such patents and publications as U.S. Pat. Nos. 2,600,788, 2,369,489, 2,343,703, 2,311,082, 2,673,801, 3,152,896, 3,519,429, 3,061,432, 3,062,653, 3,725,067, 2,908,573 and "Farbkuppler-eine Literaturubersicht," published in Agfa Mitteilungen, Band II, pp. 126–156 (1961).

Couplers which form yellow dyes upon reaction with oxidized color developing agent are acylacetanilides such as benzoylacetanilides and pivalylacetanilides. Representative couplers are described in the following patents and publications: U.S. Pat. Nos. 2,875,057, 2,407,210, 3,265,506, 2,298,443, 3,048,194, 3,447,928 and "Farbkuppler-eine Literaturubersicht," published in Agfa Mitteilungen, Band II, pp. 112–126 (1961).

When intended for incorporation in photographic elements, couplers are commonly dispersed therein with the aid of a high boiling organic solvent, referred to as a coupler solvent. Couplers are rendered nondiffusible in photographic elements, and compatible with coupler solvents, by including in the coupler molecule a group referred to as a ballast group. This group normally is located on the coupler in a position other than the coupling position and imparts to the coupler sufficient bulk to render the coupler nondiffusible in the element as coated and during processing. It will be appreciated that the size and nature of the ballast group will depend upon the bulk of the unballasted coupler and the presence of other substituents on the coupler.

In a developed photographic element, only the dye image is needed. Therefore, anything which will reduce the amount of silver halide and/or dye-forming coupler needed to obtain the desired photographic speed and tone reproduction characteristics will reduce the manufacturing cost. It has been discovered that certain organosilanes when incorporated together with couplers in photographic silver halide materials will increase the image dye yield, in some instances by at least ten percent.

British Patent Application No. 2,061,540A, and U.S. Pat. Nos. 4,264,720, 4,266,020 and 4,346,165 relate to the use of organic compounds containing silyl groups as dye image stabilizers. The organosilanes used in this invention are structurally different from those compounds, however, and are used for a different purpose.

It would be desirable to provide organosilane compounds which would improve the density and contrast of dye images obtained by color development.

These and other objects are achieved in accordance with this invention which comprises a photographic element comprising a support having thereon at least one silver halide emulsion layer having associated therewith a dye-forming coupler and an organosilane, nonhydrolyzable in an alkaline medium, wherein:

(a) one or two aryloxy groups are attached to the silicon atom of the silane either directly or indirectly through an alkylene group or an alkyleneoxy group, and (b) each aryloxy group is attached directly or indirectly through a single linking group to an aryl group substituted with a hydroxy, hydroxyalkoxy, organosilyloxy, organosilylalkoxy or organosilyloxyalkoxy group.

By requiring the organosilane to be non-hydrolyzable in an alkaline medium, certain structural limitations are necessarily inherent. For example, the substituents on the silicon atom of the silane must provide sufficient steric hindrance to prevent hydrolysis. Also, when the silicon atom is attached to an aryloxy group indirectly through an alkylene group, the alkylene group should contain either one or more than two carbon atoms, since a silylethoxy group attached to an electron-deficient aryl group is readily hydrolyzed. Further, whether or not an organosilane is hydrolyzable depends on whether or not the compound decomposed in an aqueous environment at a pH greater than 7. Such limitations are well known to those skilled in the art.

In a preferred embodiment of the invention, the organosilane compound has the formula:

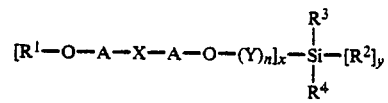

wherein:

A is a substituted or unsubstituted aryl group;

X is a chemical bond directly linking the two A groups or a divalent linking group having no more than three atoms;

Y is an alkylene group having either one or more than 2 carbon atoms or an alkyleneoxy group;

$R^1$ is H, $HO(CH_2)_m—$ or $R^2R^3R^4Si(Y)_n—$;

$R^2$, $R^3$ and $R^4$ are each independently substituted or unsubstituted alkyl, cycloalkyl or aryl groups, with the proviso that when n is 0, at least one of $R^2$, $R^3$ and $R^4$ is a branched alkyl group, a substituted cycloalkyl group or a substituted aryl group;

m is an integer from about 2 to about 10;

n is 0 or 1;

x is 1 or 2; and y is 0 or 1, with the proviso that the sum of x and y is 2.

The aryl groups represented by A, which are preferably phenyl groups, may be substituted with, for example, alkyl, aryl, acyl and sulfonyl groups, and halogen atoms. In a preferred embodiment, A is

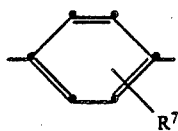

and each $R^7$ is independently hydrogen, an alkyl group having from 1 to about 6 carbon atoms, an aryl group having from about 6 to about 18 carbon atoms or a halogen atom.

The linking group X has no more than three, and preferably has one or two atoms separating the linked A groups. Examples of suitable linking groups include —$SO_2$—, —SO—, —S—, —O—, —CO—, —COO—, —OCOO—, —CONH—, —OCONH—, —$SO_2$NH— or —$CR^5R^6$, wherein each $R^5$ and $R^6$ independently is hydrogen, alkyl or aryl.

When Y is present, it is preferably an alkylene group having either 1 or from 3 to about 8 carbon atoms. Also, $R^1$ is preferably a hydrogen atom.

In a preferred embodiment, $R^2$, $R^3$ and $R^4$ are each independently a substituted or unsubstituted alkyl group having from 1 to about 16 carbon atoms, a substituted or unsubstituted cycloalkyl group having from about 3 to about 6 carbon atoms or a substituted aryl group having from about 6 to about 18 carbon atoms. When $R^2$, $R^3$ and $R^4$ form part of a silyloxy group, at least one of the groups is a branched alkyl group, e.g., i-propyl or t-butyl, a substituted cycloalkyl group, e.g., methylcyclohexyl, or a substituted aryl group, e.g., t-butylphenyl. Suitable substituents for $R^2$, $R^3$ and $R^4$ include alkyl, aryl and sulfonyl groups and halogen atoms.

Particular examples of organosilanes used in the invention have the following structures:

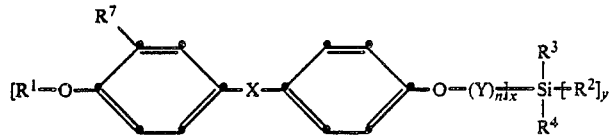

| Cmpd. No. | $R^1$ | $R^7$ | X | Y | n | x | $R^2$ | $R^3$ | $R^4$ | y |
|---|---|---|---|---|---|---|---|---|---|---|
| 1 | H | H | $SO_2$ | — | 0 | 1 | t-$C_4H_9$ | $CH_3$ | $CH_3$ | 1 |
| 2 | HO($CH_2$)$_2$ | H | $SO_2$ | — | 0 | 1 | t-$C_4H_9$ | $CH_3$ | $CH_3$ | 1 |
| 3 | $R^2R^3R^4$Si | H | $SO_2$ | — | 0 | 1 | t-$C_4H_9$ | $CH_3$ | $CH_3$ | 1 |
| 4 | H | H | $SO_2$ | — | 0 | 1 | t-$C_4H_9$ | $C_6H_5$ | $C_6H_5$ | 1 |
| 5 | HO($CH_2$)$_2$ | H | $SO_2$ | — | 0 | 1 | t-$C_4H_9$ | $C_6H_5$ | $C_6H_5$ | 1 |
| 6 | H | H | $SO_2$ | — | 0 | 1 | i-$C_3H_7$ | i-$C_3H_7$ | i-$C_3H_7$ | 1 |
| 7 | HO($CH_2$)$_2$ | H | $SO_2$ | — | 0 | 1 | i-$C_3H_7$ | i-$C_3H_7$ | i-$C_3H_7$ | 1 |
| 8 | H | H | $SO_2$ | — | 0 | 2 | — | t-$C_4H_9$ | t-$C_4H_9$ | 0 |
| 9 | H | H | $SO_2$ | $CH_2$ | 1 | 1 | $CH_3$ | $CH_3$ | $CH_3$ | 1 |
| 10 | HO($CH_2$)$_2$ | H | $SO_2$ | $CH_2$ | 1 | 1 | $CH_3$ | $CH_3$ | $CH_3$ | 1 |
| 11 | H | H | $SO_2$ | ($CH_2$)$_3$ | 1 | 1 | $CH_3$ | $CH_3$ | $CH_3$ | 1 |
| 12 | H | H | CO | — | 0 | 1 | t-$C_4H_9$ | $CH_3$ | $CH_3$ | 1 |
| 13 | H | H | C($CH_3$)$_2$ | — | 0 | 1 | t-$C_4H_9$ | $CH_3$ | $CH_3$ | 1 |
| 14 | H | H | S | — | 0 | 1 | t-$C_4H_9$ | $CH_3$ | $CH_3$ | 1 |
| 15 | H | H | SO | — | 0 | 1 | t-$C_4H_9$ | $CH_3$ | $CH_3$ | 1 |
| 16 | $R^2R^3R^4$Si | H | $SO_2$ | ($CH_2$)$_2$O | 1 | 1 | i-$C_3H_7$ | i-$C_3H_7$ | i-$C_3H_7$ | 1 |
| 17 | HO($CH_2$)$_2$ | H | $SO_2$ | — | 0 | 1 | t-$C_4H_9$ | $C_6H_5$ | $C_6H_5$ | 1 |
| 18 | H | Br | $SO_2$ | — | 0 | 1 | t-$C_4H_9$ | $CH_3$ | $CH_3$ | 1 |

As described in detail hereinafter in the specific examples of the preparation of compounds of the invention, the organosilanes may be made by reacting a halosilane with a compound comprising a first aryl group attached directly or indirectly through a single linking group to a second aryl group wherein the aryl groups are substituted with a hydroxyl group at each intended point of attachment of a silyl group. The reaction provides a compound having at least one silyl group attached directly or indirectly through an alkylene or alkyleneoxy group to an aryloxy group. The halosilane is chosen to provide the optional alkylene or alkyleneoxy link between the silyl group and the aryloxy group. Further, a halosilane having two halogen atoms can be used to provide a compound having two aryloxy groups attached directly or indirectly to the silicon atom of the silane. The halosilane is conveniently a chlorosilane. When a free hydroxyl group is required in the final product, this group can be protected during the reaction and then regenerated.

The organosilane is used in an amount sufficient to enhance dye formation, e.g., from about 0.25 to about 2.0 moles per mole of coupler, preferably from about 0.5 to about 1.0 mole per mole of coupler.

Typically, the organosilane compound and coupler are incorporated in a silver halide emulsion and the emulsion coated on a support to form a photographic element. Alternatively, the organosilane compound and coupler can be incorporated in photographic elements adjacent to the silver halide emulsion where, during development, the coupler will be in reactive association with development products such as oxidized color developing agent. Thus, as used herein, the term "associated therewith" signifies that the organosilane and coupler are in the silver halide emulsion layer or in an adjacent location where, during processing, they will be capable of reacting with silver halide development products.

Photographic elements of the invention can be single color elements or multicolor elements. Multicolor elements contain dye image-forming units sensitive to each of the three primary regions of the visible spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer, e.g., as by the use of microvessels as described in Whitmore U.S. Pat. No. 4,362,806 issued Dec. 7, 1982.

A typical multicolor photographic element of the invention comprises a support having thereon a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler and a yellow dye image-forming unit comprising at least one blue-sensitive silver halide emulsion layer having associated therewith at least one yellow dye-forming coupler, at least one of the couplers in the element containing an organosilane compound according to this invention. The element can contain additional layers, such as filter layers, interlayers, overcoat layers, subbing layers, and the like.

Another aspect of the invention relates to a process of improving the density and contrast of a photographic dye image comprising photographically processing a photographic element as described above. The specific processing steps which are used are described hereinafter.

In the following discussion of suitable materials for use in the emulsions and elements of this invention, reference will be made to *Research Disclosure*, December 1978, Item 17643, published by Industrial Opportunities Ltd., Homewell Havant, Hampshire, PO9 1EF, U.K., the disclosures of which are incorporated herein by reference. This publication will be identified hereafter by the term "Research Disclosure".

The silver halide emulsions employed in the elements of this invention can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

In addition to the couplers generally described above, the elements of the invention can include additional couplers as described in Research Disclosure Section VII, paragraphs D, E, F and G and the publications cited therein. These couplers can be incorporated in the elements and emulsions as described in Research Disclosure Section VII, paragraph C and the publications cited therein.

The photographic elements of this invention or individual layers thereof, can contain brighteners (see Research Disclosure Section V), antifoggants and stabilizers (see Research Disclosure Section VI), antistain agents and image dye stabilizers (see Research Disclosure Section VII, paragraphs I and J), light absorbing and scattering materials (see Research Disclosure Section VIII), hardeners (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents useful in the invention are p-phenylene diamines. Especially preferred are 4-amino-3-methyl-N,N-diethylaniline hydrochloride, 4-amino-3-methyl-N,N-diethylaniline hydrochloride, 4-amino-3-methyl-N-ethyl-N-β-(methanesulfonamide)ethylaniline sulfate hydrate, 4-amino-3-methyl-N-ethyl-N-β-hydroxyethylaniline sulfate, 4-amino-3-β-(methane-sulfonamido)ethyl-N,N-diethylaniline hydrochloride and 4-amino-3-methyl-N-ethyl-N-(2-methoxyethyl)aniline-di-p-toluenesulfonic acid.

With negative working silver halide, the processing step described above gives a negative image. To obtain a positive (or reversal) image, this step can be preceded by development with a non-chromogenic developing agent to develop exposed silver halide, but not form dye, and then uniformly fogging the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The following examples are included for a further understanding of this invention.

PREPARATION EXAMPLE 1

Preparation of Compound 1

(a) Preparation of 4-(4-benzyloxyphenylsulphonyl)phenoxy-t-butyl-dimethyl silane The compound of formula (100 mmol, 34 g):

was dissolved with t-butylchlorodimethyl silane (100 mmol, 15 g) in dimethyl formamide (70 ml). Imidazole (250 mmol, 17 g) was then added and the mixture was stirred at 40° C. for 16 hours. It was then poured into of water (1000 ml), extracted with three 150 ml quantities of ethyl acetate, and the extract washed with two 100 ml quantities of 2M aqueous sodium hydroxide, 100 ml of water and dried. The ethyl acetate was then evaporated off to leave a crude product which was recrystallized from ethanol.

(b) Debenzylation

The product of part (a) (78 mmol) was dissolved in ethyl acetate (250 ml) and palladium on charcoal (0.1 weight equivalents) (Pd=10% by weight based on the weight of the charcoal) was added. The mixture was hydrogenated overnight at 20–30 atmosphere pressure and 50°–60° C. The charcoal was removed by filtering through kieselguhr, the ethyl acetate was evaporated off, and the product was then purified by recrystallization to give 57 mmol of product having a melting point of 114°–6° C. The yield of product was 73%.

PREPARATION EXAMPLE 2

Preparation of Compounds 4, 6, 9 and 11

The following additional compounds were made by the methods described in parts (a) and (b) of Example 1. In carrying out part (a) of the synthesis, 100 mmol of the appropriate substituted silane was used.

TABLE 1

| Compound | Silane | Yield, % | M.Pt. °C. |
| --- | --- | --- | --- |
| 4 | ClSi(C$_6$H$_5$)$_2$C$_4$H$_9$—t | 86 | 117–9 dec |
| 6 | ClSi(C$_3$H$_7$—i)$_3$ | 88 | 129–137 |
| 9 | ClCH$_2$Si(CH$_3$)$_3$ | 80 | 152–3 |
| 11 | CH$_3$C$_6$H$_5$SO$_2$O(CH$_2$)$_3$Si(CH$_3$)$_3$ | 84 | viscous oil |

PREPARATION EXAMPLE 3

Preparation of Compound 3

A bis(trialkylsilylether) (compound 3) was prepared by reacting 4,4'-dihydroxyphenylsulphone with a twice molar quantity of t-butylchlorodimethylsilane using reaction conditions similar to those described in part (a) of Example 1. A yield of 58% was obtained, and the purified product had a melting point of 130°–2° C.

PREPARATION EXAMPLE 4

Preparation of Compounds 12 and 13

Mixtures of mono- and bis-silylethers, for subsequent separation, were prepared by reacting a starting compound of the general formula:

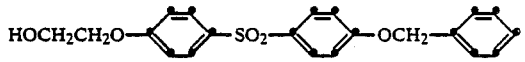

wherein X is —CO or —C(CH$_3$)$_2$— with t-butylchlorodimethylsilane. The reactants were dissolved in dimethylformamide and imidazole was then added. The reaction mixture was kept at room temperature for 16 hours and the products then separated by column chromatography. The yields and melting points of the purified compounds are given in Table 2.

TABLE 2

| Compound | X | Silylether Groups | Yield, % | M.Pt. °C. |
| --- | --- | --- | --- | --- |
| 12 | —CO— | 1 | 45 | 96–8 |
|  | —CO— | 2 | 19 | 53–6 |
| 13 | —C(CH$_3$)$_2$— | 1 | 46 | 87–8 |
|  | —C(CH$_3$)$_2$— | 2 | 16 | 48–9 |

PREPARATION EXAMPLE 5

Preparation of Compound 8

Compound 8 was prepared from the starting compound used in Example 1(a) by reaction with half the molar quantity of di-t-butyldichlorosilane. The reaction was carried out in dimethylformamide at room temperature in the presence of imidazole. After 16 hours, the product was debenzylated by reduction with hydrogen in the presence of palladium carbon catalyst for 8 hours at 50° C. The yield was 54% and the product had a melting point of 150° C.

PREPARATION EXAMPLE 6

Preparation of Compounds 2, 5, 7 and 10

4-(4-Benzyloxyphenylsulphonyl)phenol was reacted for 4 hours at 160° C. with ethylene carbonate in the presence of tetra-n-butylammonium bromide. The product, of formula:

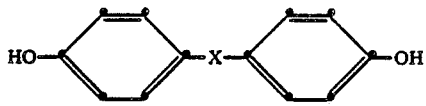

was debenzylated by reduction for 16 hours at 60° C. with hydrogen when dissolved in tetrahydrofuran containing suspended palladium-carbon catalyst. The debenzylated compound was then reacted with chlorosilanes to give various organosilanes as shown in Table 3.

TABLE 3

| Compound | Chlorosilane | Yield, % | M.Pt. °C. |
| --- | --- | --- | --- |
| 2 | ClSi(CH$_3$)$_2$C$_4$H$_9$—t | 62 | 107–10 |
| 5 | ClSi(C$_6$H$_5$)$_2$C$_4$H$_9$—t | 73 | oil |
| 7 | ClSi(i-C$_3$H$_7$)$_3$ | 25 | gum |
| 10 | ClCH$_2$Si(CH$_3$)$_3$ | 75 | 88–95 |

EXAMPLE 1

The photographic effects of various organosilanes of the invention were measured as described below. The coupler used was the yellow dye-forming coupler of the formula:

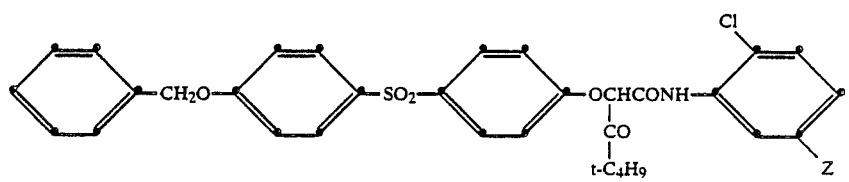

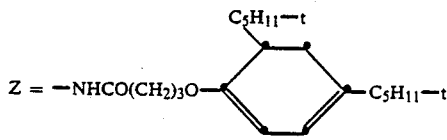

A dispersion of the coupler, a coupler solvent and the organosilane to be tested was made in aqueous gelatin solution. The amounts of the constituents were as follows:

| | |
|---|---|
| Coupler | 11.3 g (12.4 mmol) |
| Coupler solvent (dibutylphthalate) | 5.6 g |
| Organosilane compound | 6.2 mmol |
| 10% w/v aqueous gelatin | 70.5 g |
| water to make: | 150 g |

A control dispersion was made which did not contain an organosilane.

An auxiliary solvent and a surfactant were used to assist the dispersion step which was carried out in a homogenizer.

The various dispersions were mixed with a silver chlorobromide photographic emulsion and coated on a resin-coated paper support. A supercoat of hardened gelatin was also applied to give a coating of the following composition.

| Gelatin 1 g/m² | |
|---|---|
| Coupler | 1.0 g/m² (1.1 mmol) |
| Coupler solvent | 0.5 g/m² |
| Organosilane compound | 0.55 mmol |
| Gelatin | 1.4 g/m² |
| Silver halide | 3.5 mmol/m² |
| Support | |

A sample of each coating was exposed to a sensitometric wedge for 0.1 sec and then processed in a standard color print process using a color developer containing the color developing agent 4-N-ethyl-N-(β-methanesulphonamidoethyl)amino-o-toluidine sesquisulphate and a bleach-fix solution. The wedge image was densitometrically assessed and the contrast and log speed, relative to the control, values are tabulated below.

TABLE 4

| Compound No. | Rel. Log Speed Increase (D = 1.0) | Contrast | Control Contrast |
|---|---|---|---|
| 1 | 0.08 | 2.82 | 2.41 |
| 2 | 0.10 | 3.04 | 2.60 |
| 4 | 0.07 | 2.69 | 2.41 |
| 5 | 0.05 | 2.81 | 2.32 |

TABLE 4-continued

| Compound No. | Rel. Log Speed Increase (D = 1.0) | Contrast | Control Contrast |
|---|---|---|---|
| 6 | −0.01 | 2.94 | 2.41 |
| 8 | 0.08 | 2.93 | 2.60 |
| 9 | 0.06 | 2.90 | 2.41 |
| 10 | 0.07 | 3.02 | 2.60 |
| 12 | 0.06 | 2.74 | 2.60 |
| 18 | 0.05 | 2.82 | 2.32 |

It is evident from these results that all the compounds gave a significant increase in contrast, and only Compound 6 did not give a slight speed increase at D=1.0. However, Compound 6 did produce a slight speed increase at higher density.

EXAMPLE 2

The magenta dye-forming coupler of the following formula was used:

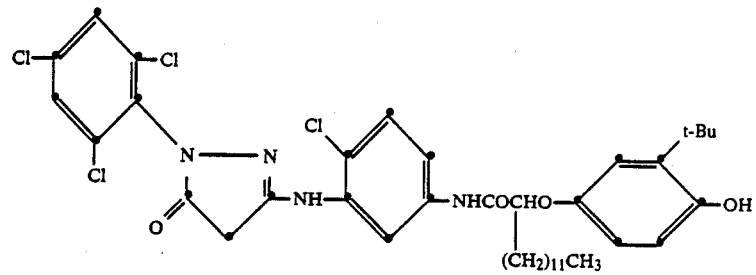

A dispersion of the coupler was made up in a way similar to that described in Example 1. The amounts of the constituents were as follows:

| | |
|---|---|
| Coupler | 2.0 g |
| Coupler Solvent (dibutyl phthalate) | 2.0 g |
| Compound No. 1 | 0.85 g |
| 10% w/v aqueous gelatin | 40.0 g |
| Water to make | 50.0 g |

Auxiliary solvent and surfactant were used as before and the dispersions were mixed with a silver chlorobromide photographic emulsion and coated on a transparent support. A supercoat of hardened gelatin was applied to give a coating of the following composition:

| Gelatin 1.07 g/m² | |
|---|---|
| Coupler | 0.69 mmol/m² (0.54 g/m²) |
| Coupler solvent | 0.54 g/m² |
| Compound No. 1 | 0.69 mmol/m² (0.25 g/m²) |
| Gelatin | 3.22 g/m² |
| Silver halide | 0.54 g/m² |
| Support | |

The coating was exposed and processed in accordance with the procedure of Example 1.

The contrast and log speed, relative to the control, values are shown below.

|  | Contrast | Rel. Log Speed Increase (D = 1.0) |
|---|---|---|
| Control | 1.51 |  |
| Compound 1 | 1.74 | 0.14 |

Compound 1 again gave an increase in contrast as well as speed.

The invention has been described in detail with particular reference to preferred embodiments thereof, but it will be understood that variations and modifications can be effected within the spirit and scope of the invention.

What is claimed is:

1. A photographic element comprising a support having thereon at least one silver halide emulsion layer having associated therewith a dye-forming coupler and an organosilane, nonhydrolyzable in an alkaline medium, wherein:
   (a) one or two aryloxy groups are attached to the silicon atom of the silane either directly or indirectly through an alkylene group or an alkyleneoxy group,
   (b) each said aryloxy group is attached directly or indirectly through a single linking group to an aryl group substituted with a hydroxy, hydroxyalkoxy, organosilyloxy, organosilylalkoxy or organosilyloxyalkoxy group, and
   (c) in the event that at least one of said aryloxy groups is directly attached to the silicon atom of said silane, then said silicon atom must also be substituted by at least one branched alkyl group, substituted cycloalkyl group or substituted aryl group.

2. The photographic element of claim 1 wherein said organosilane has the formula:

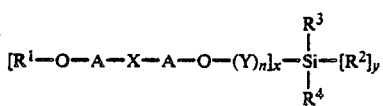

wherein:
A is a substituted or unsubstituted aryl group;
X is a chemical bond directly linking the two A groups or a divalent linking group having no more than three atoms;
Y is an alkylene group having either one or more than 2 carbon atoms or an alkyleneoxy group;
$R^1$ is H, $HO(CH_2)_m$— or $R^2R^3R^4Si(Y)_n$—;
$R^2$, $R^3$ and $R^4$ are each independently substituted or unsubstituted alkyl, cycloalkyl or aryl groups, with the proviso that when n is 0, at least one of $R^2$, $R^3$ and $R^4$ is a branched alkyl group, a substituted cycloalkyl group, or a substituted aryl group;
m is an integer from about 2 to about 10;
n is 0 or 1;
x is 1 or 2; and
y is 0 or 1, with the proviso that the sum of x and y is 2.

3. The photographic element of claim 2 wherein each A is a substituted or unsubstituted phenyl group.

4. The photographic element of claim 3 wherein each A is

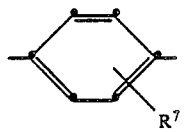

and each $R^7$ is independently hydrogen, an alkyl group having from 1 to about 6 carbon atoms, an aryl group having from about 6 to about 18 carbon atoms or a halogen atom.

5. The photographic element of claim 2 wherein X is —$SO_2$—, —SO—, —S—, —O—, —CO—, —COO—, —OCOO—, —CONH—, —OCONH—, —$SO_2$NH— or —$CR^5R^6$, wherein each $R^5$ and $R^6$ independently is hydrogen, alkyl or aryl.

6. The photographic element of claim 2 wherein $R^2$, $R^3$ and $R^4$ are each independently a substituted or unsubstituted alkyl group having from 1 to about 16 carbon atoms, a substituted or unsubstituted cycloalkyl group having from about 3 to about 6 carbon atoms or a substituted or unsubstituted aryl group having from about 6 to about 18 carbon atoms.

7. The photographic element of claim 2 wherein said organosilane is present in an amount of from about 0.25 to about 2.0 moles per mole of coupler.

8. A process of improving the density and contrast of a photographic dye image comprising processing a photographic element comprising a support having thereon at least one silver halide emulsion layer having associated therewith a dye-forming coupler in the presence of an organosilane, nonhydrolyzable in an alkaline medium, wherein:
   (a) one or two aryloxy groups are attached to the silicon atom of the silane either directly or indirectly through an alkylene group or an alkyleneoxy group,
   (b) each said aryloxy group is attached directly or indirectly through a single linking group to an aryl group substituted with a hydroxy, hydroxyalkoxy, organosilyloxy, organosilylalkoxy or organosilyloxyalkoxy group, and
   (c) in the event that at least one of said aryloxy groups is directly attached to the silicon atom of said silane, then said silicon atom must also be substituted by at least one branched alkyl group, substituted cycloalkyl group or substituted aryl group.

9. The process of claim 8 wherein said organosilane has the formula:

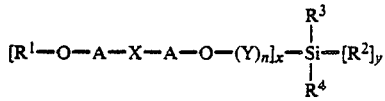

wherein:
A is a substituted or unsubstituted aryl group;
X is a chemical bond directly linking the two A groups or a divalent linking group having no more than three atoms;
Y is an alkylene group having either one or more than 2 carbon atoms or an alkyleneoxy group;
$R^1$ is H, $HO(CH_2)_m$— or $R^2R^3R^4Si(Y)_n$—;
$R^2$, $R^3$ and $R^4$ are each independently substituted or unsubstituted alkyl, cycloalkyl or aryl groups, with the proviso that when n is 0, at least one of $R^2$, $R^3$ and $R^4$ is a branched alkyl group, a substituted cycloalkyl group, or a substituted aryl group;

m is an integer from about 2 to about 10;

n is 0 or 1;

x is 1 or 2; and y is 0 or 1, with the proviso that the sum of x and y is 2.

10. The process of claim 9 wherein each A is a substituted or unsubstituted phenyl group.

11. The process of claim 10 wherein each A is

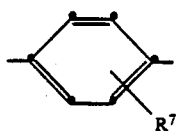

and each $R^7$ is independently hydrogen, an alkyl group having from 1 to about 6 carbon atoms, an aryl group having from about 6 to about 18 carbon atoms or a halogen atom.

12. The process of claim 9 wherein X is $-SO_2-$, $-SO-$, $-S-$, $-O-$, $-CO-$, $-COO-$, $-CONH-$, $-OCONH-$, $-SO_2NH-$ or $-CR^5R^6$, wherein each $R^5$ and $R^6$ independently is hydrogen, alkyl or aryl.

13. The process of claim 9 wherein $R^2$, $R^3$ and $R^4$ are each independently a substituted or unsubstituted alkyl group having from 1 to about 16 carbon atoms, a substituted or unsubstituted cycloalkyl group having from about 3 to about 6 carbon atoms or a substituted or unsubstituted aryl group having from about 6 to about 18 carbon atoms.

14. The process of claim 9 wherein said organosilane is present in an amount of from about 0.25 to about 2.0 moles per mole of coupler.

* * * * *